United States Patent [19]

Ajello

[11] Patent Number: 5,054,610
[45] Date of Patent: Oct. 8, 1991

[54] DISPOSABLE SINGLE-USE CONTACT LENS CONDITIONING PACKAGE

[75] Inventor: Marc Ajello, Atlanta, Ga.

[73] Assignee: Ciba-Geigy Corporation, Ardsley, N.Y.

[21] Appl. No.: 359,720

[22] Filed: May 31, 1989

[51] Int. Cl.⁵ .............................................. B65D 81/24
[52] U.S. Cl. ..................................... 206/5.1; 206/205; 206/210; 206/229; 206/461; 206/820; 220/314; 220/324
[58] Field of Search ............... 206/5.1, 205, 210, 212, 206/213, 229, 230, 531, 461, 820; 134/137, 143; 220/314, 324

[56] References Cited

U.S. PATENT DOCUMENTS

| | | | |
|---|---|---|---|
| 3,314,533 | 4/1967 | Kopfle | 206/5.1 |
| 3,369,656 | 2/1968 | Skinner, Jr. | 206/205 |
| 3,722,779 | 3/1973 | Chang | 206/229 |
| 3,941,248 | 3/1976 | Moser et al. | 206/531 |
| 4,223,788 | 9/1980 | Jaeger et al. | 220/314 |
| 4,423,809 | 1/1984 | Mazzocco | 206/5.1 |
| 4,568,517 | 2/1986 | Kaspar et al. | 134/143 |
| 4,691,820 | 9/1987 | Martinez | 206/461 |

Primary Examiner—David T. Fidei
Attorney, Agent, or Firm—Wenderoth, Lind & Ponack

[57] ABSTRACT

A disposable single-use contact lens conditioning package having two pairs of adjacent open-topped containers of a size for accommodating a contact lens to be conditioned, a contact lens sterilizing solution or cleaning member in one container of each pair, a solution for counteracting the sterilizing solution or rinsing away a lens cleaning liquid in the other container of each pair, and a cover sealed over the pairs of containers over the tops thereof and capable of being peeled off the containers for opening the tops of the containers.

7 Claims, 4 Drawing Sheets

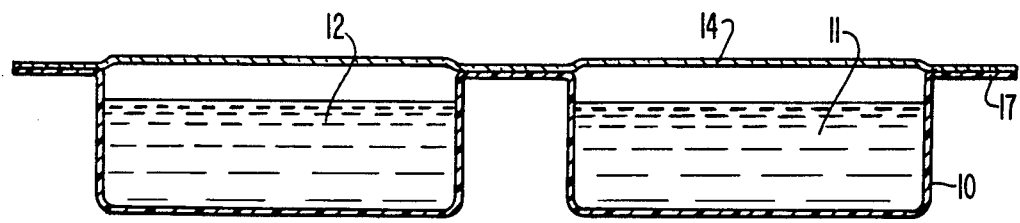
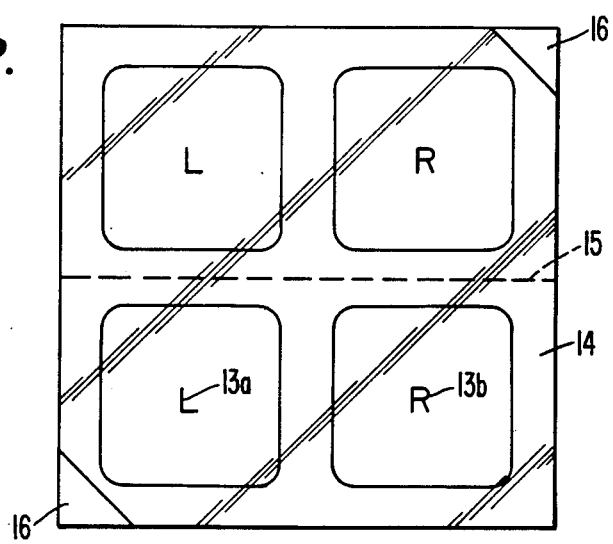
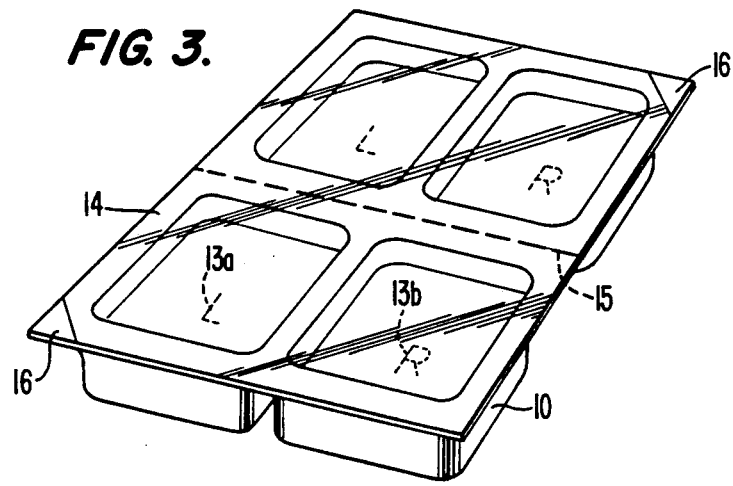

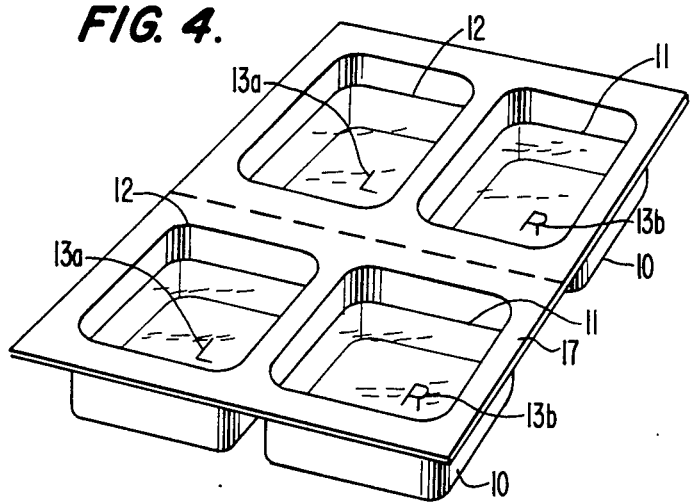
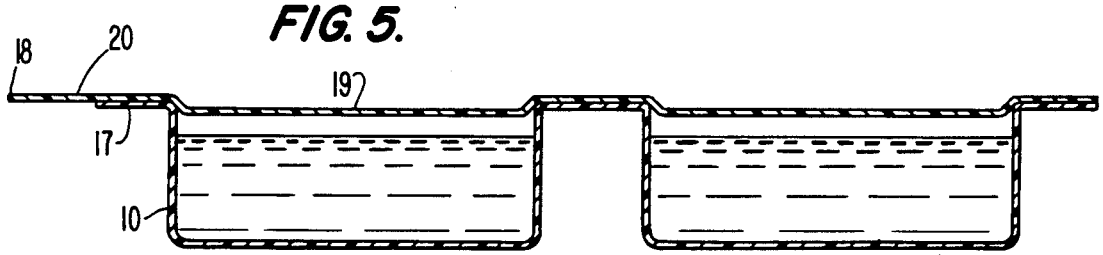
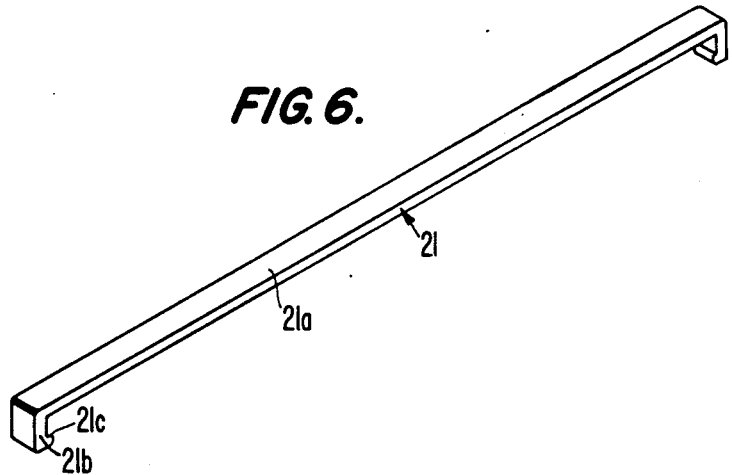
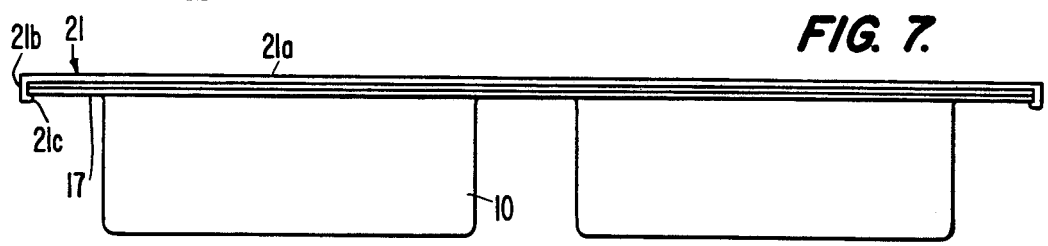

DISPOSABLE SINGLE-USE CONTACT LENS CONDITIONING PACKAGE

The present invention relates to a disposable single-use personal article conditioning package, and more particularly to such a package which is for use in cleaning or sterilizing contact lenses and the like.

BACKGROUND OF THE INVENTION

Since the advent of contact lenses, it has been the practice to store the lenses in container-like lens storage devices. In the case of the so-called soft contact lenses, the practice has been to provide for the use of a disinfecting or sterilizing solution, and/or a rinsing solution which can be poured into and out of the storage device for cleaning the lenses, disinfecting the lenses, and then rinsing the disinfecting solution from the lenses, or neutralizing the disinfecting solution remaining on the lenses. In the case of the hard lenses, it is only necessary to provide a cleaning means, such as a sponge or cloth impregnated with a detergent or the like, and some sort of rinsing solution to remove the cleaner.

Recently, a sterilizing or disinfecting treatment for soft contact lenses has been proposed, which utilizes an aqueous hydrogen peroxide solution as a sterilizing or disinfecting solution, and following the immersion of the lenses in such a solution, and the removal from such solution, the lenses are immersed in a neutralizing solution to turn the residual disinfecting solution into a saline solution. This is accomplished by, for example, using a neutralizer which decomposes the residual hydrogen peroxide into oxygen and water, the neutralizer containing a salt, which makes the resulting water saline. Examples of such a system are shown in U.S. Pat. Nos. 4,521,375 and 4,568,517. Another recently developed system of the same type provides, as the sterilizing solution, a saline hydrogen peroxide solution, and the container-like device is provided with a catalyst, for example platinum, so that when the hydrogen peroxide and salt solution is poured into the device, the platinum, acting as a catalyst, decomposes the hydrogen peroxide into water and oxygen, leaving the saline solution as the storage solution.

These systems, for both soft and hard lenses, have, to date, been used with containers which, after they have been used, are cleaned out, by rinsing with water, for example, and then reused over and over again. There is some danger of a buildup of microorganisms in the containers which is particularly bad where the soft lenses are being treated.

It is desirable, however, to provide for a single-use package which can be used once and then discarded. This is very useful, for example, for persons who are traveling, or persons who need to clean, sterilize or disinfect their contact lenses when they are away from the place where the reusable container device is kept.

OBJECTS AND BRIEF SUMMARY OF THE INVENTION

It is an object of the present invention to provide a contact lens conditioning package which includes, in the form in which it is sold, a lens conditioning means, such as a lens cleaning means or sterilizing or disinfecting solution, and which can be used one time for cleaning, disinfecting or sterilizing contact lenses, and then discarded.

It is a further object of the present invention to provide such a contact lens conditioning package which is simple to use, and inexpensive to produce, yet which can be used so as to carry out the cleaning, disinfecting or sterilizing to the desired degree.

It is a still further object of the present invention to provide an assembly of a plurality of such lens conditioning packages separably attached to each other, so that they can be removed one at a time and used and then discarded.

As indicated above, the conditioning means can be the solution which is used to treat the soft contact lenses, which solution can be a sterilizing solution or a disinfecting solution, which, in the art, are technically different. However, in the following specification, the term "sterilizing solution" will be used as a term which is generic to both sterilizing and disinfecting solutions. The term "conditioning means" will be used as a term which is generic to such a sterilizing solution and to a cleaning means. Similarly, as indicated above, the solution used to treat the contact lenses after they have been conditioned, i.e. cleaned, sterilized or disinfected, can be either a neutralizing solution, or a simple rinsing solution. Hereinafter, such a solution will be described as a conditioning-counteracting solution, i.e. it is a sterilizing solution-counteracting solution which counteracts the effects of the sterilizing solution or rinses away the disinfecting solution, or is a rinsing solution which rinses away the cleaner used in the cleaning means.

The objects of the present invention are achieved by a disposable single-use contact lens conditioning package which comprises a pair of adjacent open-topped containers of a size for accommodating contact lenses to be sterilized. A conditioning means, i.e. a cleaning means or a sterilizing solution is provided in one of the containers and a conditioning-counteracting solution is provided in the other of said containers. Cover means is provided in sealing engagement with the containers around the open tops thereof which is capable of being peeled off the containers for opening the tops of the containers.

The cover means can be two separable portions, one over a corresponding one of each of the containers, so that one container of the pair can be uncovered at a time.

The invention also includes a replacable cover fittable over the open tops of the containers for closing the containers after the cover means has been peeled off, or a cover holddown which can be fitted over the container for holding down a partially peeled back cover means portion.

Thus, the invention provides a simple package which can be made by the so-called blister pack techniques to contain a single-use amount of conditioning means and a single-use amount of neutralizing or rinsing solution, so that by peeling off the cover means, the lenses can be first cleaned, sterilized or disinfected in the one solution, and then rinsed or the sterilizing solution remaining on the lenses neutralized in the other container, after which the package can be discarded. Moreover, because the sterilizing solution is sealed in the package, and is used only once after the package is opened, buildup of undesirable microorganisms, which may take place in multi-use containers, is avoided.

While the foregoing describes the package as being usable for contact lenses, it will be clear that that it can also be used for similar personal articles, such as false teeth.

BRIEF DESCRIPTION OF THE DRAWINGS

The invention will now be described in greater detail in connection with the accompanying drawings, in which:

FIG. 1 is a sectional elevation view of a contact lens conditioning package according to one embodiment of the present invention;

FIG. 2 is a top plan view of the package as shown in FIG. 1;

FIG. 3 is a perspective view of the package of FIG. 2 with the cover means in place;

FIG. 4 is a view similar to FIG. 3 with the cover means removed, and showing the solutions in the respective containers;

FIG. 5 is a view similar to FIG. 1 but showing a replaceable cover in place on the container;

FIG. 6 is a perspective view of a cover holddown;

FIG. 7 is a view similar to FIG. 1 showing the cover holddown of FIG. 6 in place;

DETAILED DESCRIPTION OF THE INVENTION

Figure 8:
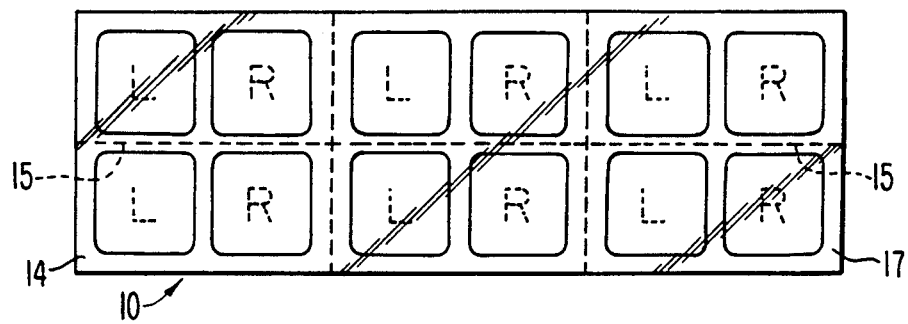
FIG. 8 is a perspective view of an assembly of packages as shown in FIGS. 1-4.

In one preferred embodiment of the present invention, which is particularly for conditioning, i.e. sterilizing, soft contact lenses, the package is a sterilizing package, which comprises a series of solution containing containers 10 which are in pairs of adjacent containers 10. In the embodiment disclosed, there are two side-by-side pairs, as shown in FIGS. 2-4.

One pocket of each pair contains a conditioning means in the form of a sterilizing solution 11, and the other pocket of each pair contains a conditioning-counteracting solution in the form of a sterilizing solution-counteracting solution 12, which can be a neutralizing solution which neutralizes the sterilizing agent, or a simple rinsing solution for rinsing the disinfecting solution from the contact lenses.

In the specific embodiment, the containers having the sterilizing solution 11 therein are side by side with corresponding containers in adjacent pairs, and the containers with the sterilizing solution-counteracting solution 12 therein are side by side with corresponding containers in adjacent pairs.

As shown in FIGS. 2-4, the containers can have indicia 13a and 13b therein, the indicia 13a, in the preferred embodiment, being a letter L, and the indicia 13b being a letter R, to indicate respectively the containers for receiving left and right contact lenses. The indicia can be either printed or otherwise formed on the surface of the bottom of the containers, or can be embossed or molded into the material of the containers.

A cover means 14 in the form of a sealing cover is placed over the containers and, in the preferred embodiment, is a flexible material sealing cover which is adhered to a flange 17 around the open tops of the containers 10, so as to seal the containers. The cover means is preferably in two separable cover portions, separable along a parting line 15, which runs between the containers of the respective pairs. As shown in FIG. 2, the line 15 is between the L containers of one pair of adjacent containers, and between the R containers of the pair of adjacent containers side by side with the L containers. Each of the cover portions has a peel-back portion 16, preferably at a corner of the corresponding container, which is not adhered to the web portion surrounding the edges of the containers, so that it can be lifted and grasped by the fingers of a user to peel the cover means 14 off the tops of the containers.

This structure is conventional blister pack structure, and is adapted to the purpose of the present invention, i.e. conditioning of contact lenses.

As seen in FIG. 3, the cover means can be transparent, but it would be obvious that the cover means could also be opaque. Similarly, the material of which the containers is made can be transparent or opaque.

In the use of the package, it will sometimes be desired to leave a lens in one or more of the containers 10 for an extended period of time, such as overnight or during a trip, and to this end it is desirable to provide a way of re-covering the containers once the cover means has been peeled back.

To this end, the invention first contemplates the provision of a replacable cover 18, as shown in FIG. 5, which has depressed portions 19 therein with a shape for fitting slightly down into the open tops of the respective containers 10, and which has a tongue 20 which projects outwardly past the edge of the web 17 around the top of the respective pockets. The tongue 20 enables the cover to be gripped and lifted, or gripped and used to place the cover into position with the depressed portions 19 fitted into the open tops of the containers for replacably closing the containers.

Alternatively, the peeled back portion of cover means 14 can be placed back in its original position and held in place by a holddown 21, as shown in FIGS. 6 and 7, which is constituted by a bar portion 21a and depending end portions 21b having a rounded snap-on bead 21 extending inwardly beneath the bar portion 21a from the lower end of the depending end portions 21b. The holddown is dimensioned so that when it is laid on top of the replaced cover portion and pressed down, the snap-on beads 21c are caused to snap past the outer ends of flanges 17 and engage under the flanges, thus holding the holddown 21 in place with the cover portion beneath it.

As will be understood, the package is used by first peeling off the portion of the sealing cover 14 which covers the containers containing the sterilizing solution 11, and soft contact lenses to be sterilized are placed into the solution 11, the left hand contact lens being placed in the container marked with the indicia 13a, and the right hand contact lens being placed in the container 10 with the indicia 13b. After the appropriate time, the remainder of the sealing cover 14 covering the containers containing the sterilizing solution-counteracting solution 12 is peeled off, and the contact lenses are removed from the first containers and placed in the second containers. The solution 12 in these containers is appropriate for either neutralizing the solution 11 in the sterilizing solution containing containers, or rinsing the solution in the sterilizing solution containing containers from the contact lenses. After the appropriate action of the solution 12 has taken place, the contact lenses are removed for insertion into the eyes, and the package is discarded.

If, during this process, it is desired to temporarily cover the containers 10, either the replacable cover 18 is used by placing it on the containers in the manner as shown in FIG. 5, or the holddown 21 is used to hold the previously peeled back cover portion in place.

It will be understood that the single package for sterilizing a pair of contact lenses as shown in FIGS. 1–4 can be formed as part of an assembly of such disposable single-use contact lens sterilizing packages, as shown in FIG. 8. In FIG. 8, the packages of FIGS. 1–4 are joined edge to edge in a convenient number so as to be detachable along a separable joint 22. In use, a pair of containers is detached, so as to provide a package as shown in FIGS. 1–4, for the desired use. At the time the next sterilization is needed, another set of pairs is removed to form another package as shown in FIGS. 1–4.

Figure 9:
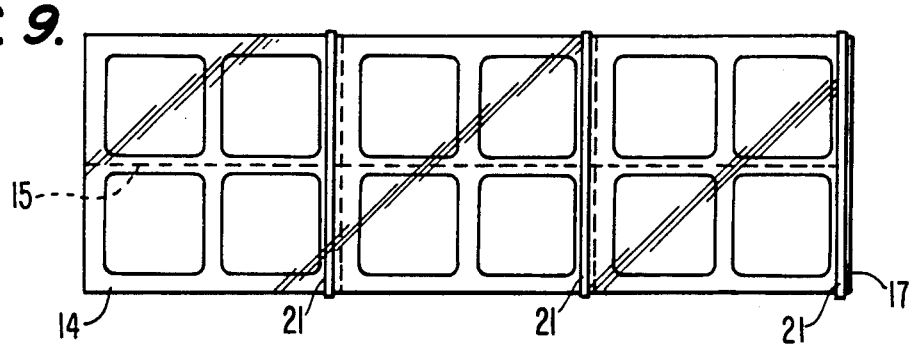
FIG. 9 is a view similar to FIG. 8 showing an assembly of packages in which the holddown bar of FIG. 6 is incorporated.

In order to make the holddown 21 readily available to the user of the sterilizing package of the present invention, it is convenient to provide the holddown in the assembly of packages as shown in FIG. 8. This is done by placing such a holddown on the flange 17 of the containers prior to placing the cover means 14 on the package so that the holddown 21 is incorporated in the package. FIG. 9 shows such an assembly of packages in which a holddown is provided for each package, being sealed under the cover means 14 just to the right of the two pairs of containers 10 which make up a single package to be detached from the assembly for use. It should of course be understood that if the packages are formed as individual packages with just the two pairs of containers 10 therein, it is also possible to seal a holddown 21 under the cover means 14 against a part of the flange 17.

Figure 10:
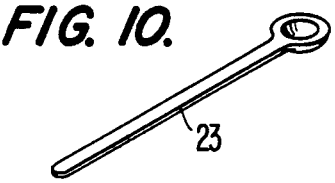
FIG. 10 is a perspective view of a lens handing implement.
Figure 11:
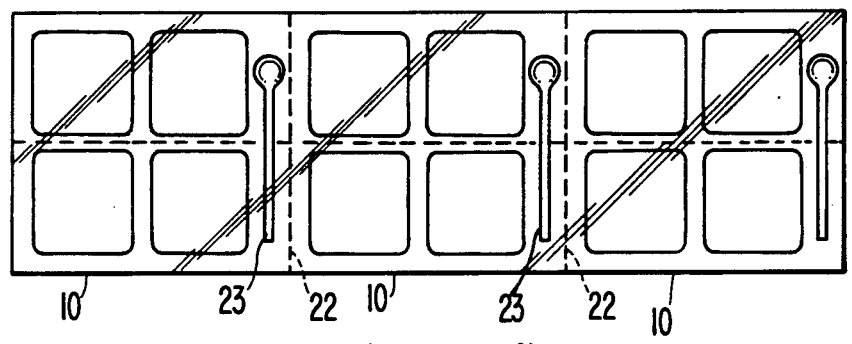
FIG. 11 is a view similar to FIG. 8 showing an assembly of packages in which the lens handling implement of FIG. 10 is incorporated.

Because it is sometimes difficult to handle soft contact lenses with the fingers, and because this may introduce undesirable microorganisms to the lenses, lens handling implements are known by which the lenses can be picked up and handled. One such implement is shown in FIG. 10 which is a perspective view of a spoon-like lens handling implement 23. FIG. 11 shows such a lens handling implement sealed under the cover means 14 of each package in an assembly of packages. As with the provision of the holddown 21 as shown in FIG. 9, the lens handling implement 23 can be provided in packages which have just the two pairs of containers 10, it is also possible to seal a lens handling implement 23 under the cover means 14 against a part of the flange 17.

Figure 12:
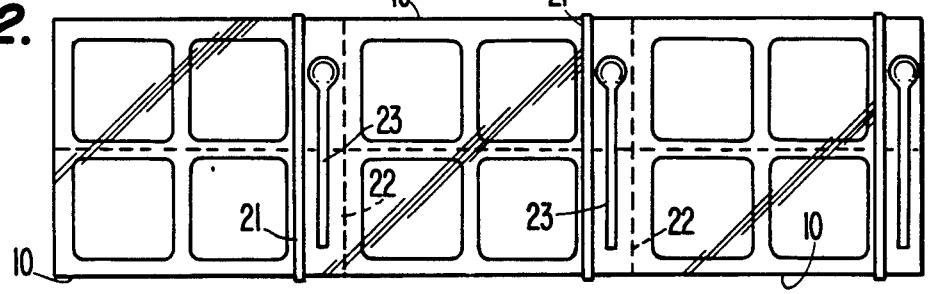
FIG. 12 is a view similar to FIG. 8 showing an assembly of packages in which both the cover holddown of FIG. 6 and the implement of FIG. 10 are incorporated.

As shown in FIG. 12, it is also possible to provide both a holddown 21 and a lens handling implement 23 in the individual packages making up the assembly. It would of course also be possible to provide both items in individual packages having just the two pairs of containers 10.

Figure 13:
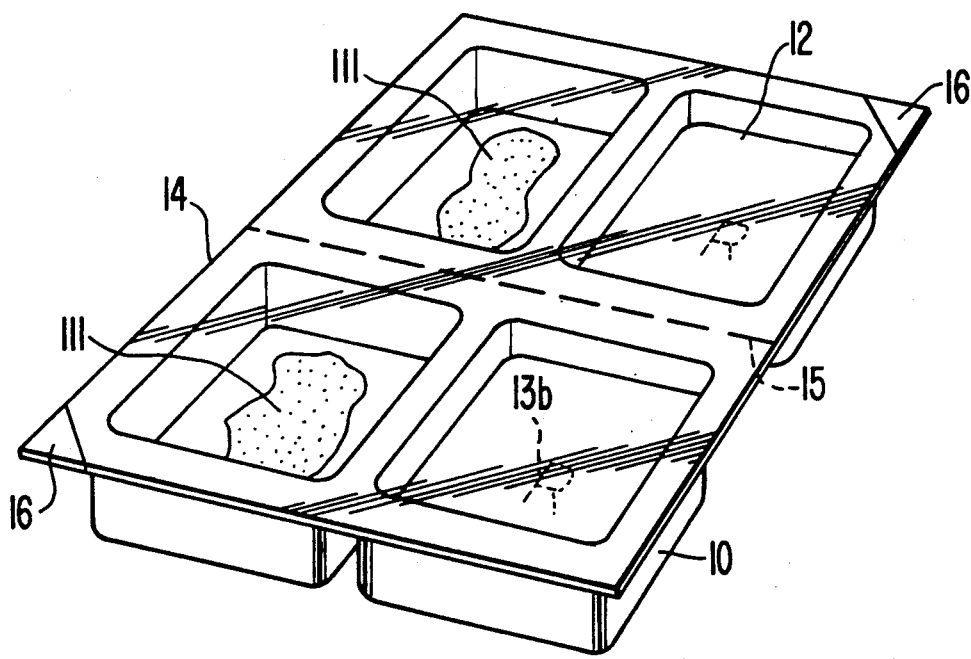
FIG. 13 is a view similar to FIG. 1 of a second embodiment of a conditioning package according to the invention.

In a second preferred embodiment of the present invention, which is particularly for conditioning, i.e. cleaning, hard contact lenses, the package is a cleaning package which comprises a series of open-topped containers 10 just like the containers 10 of the first embodiment, which are in pairs of adjacent containers 10. As in the first embodiment, there are two side-by-side pairs, as shown in FIG. 13.

One pocket of each pair contains a conditioning means in the form of a cleaning member 111, such as a piece of cloth or a sponge, soaked with a lens cleaning liquid, such as a liquid detergent. The other pocket of each pair contains a conditioning-counteracting solution 12 which is a rinsing solution for rinsing the detergent from the contact lenses.

In other respects the second embodiment is identical to the first embodiment, having the indicia 13a and 13b if desired, cover means 14, and can be assembled by conventional blister pack technology. A replacable cover like the cover 18 of of the first embodiment, and a holddown like the holddown 21 of the first embodiment can be provided. The packages can be formed as an assembly of packages just as with the packages of the first embodiment and as shown in FIGS. 8, 9, 11 and 12.

The manner of using the package of the second embodiment is basically the same as the manner of using the package of the first embodiment. The cover 14 is peeled back and the cleaning member 111 removed and used to wipe the hard contact lens clean. Then the cleaned lens is placed in the rinsing solution 12 to rinse the detergent or the like off the lenses before they are inserted in the eye of the user.

While the foregoing description has been for a package for use with contact lenses, in which the pairs of containers are in turn placed side by side with corresponding containers in other pairs, the package is adaptable for use particularly for sterilization of other personal articles, such as false teeth. For such a package, only a single pair of containers is needed, the false teeth or the like being first immersed in one of the containers which contains a sterilizing solution, and thereafter into the second adjacent container of the pair for counteracting the effect of the sterilizing solution, either by neutralizing or by rinsing.

While the invention has been described in the foregoing in terms of certain embodiments thereof, it will be understood that it is within the scope of the invention to provide other embodiments, and that the invention is limited only by the attached claims.

What is claimed is:

1. A disposable single-use contact lens conditioning package, comprising:
   two pairs of adjacent open-topped containers of a size for accommodating a contact lens to be conditioned;
   a contact lens conditioning means in one container of each pair;
   a conditioning-counteracting solution in the other container of each pair;
   cover means in sealing engagement with said pairs of containers around the open tops thereof and capable of being peeled off said containers for opening the tops of said containers; and
   a cover means holddown for holding said cover means in place over said containers, said cover means holddown being sealed under said cover means against said containers.

2. A disposable single-use contact lens conditioning package, comprising:
   two pairs of adjacent open-topped containers of a size for accommodating a contact lens to be conditioned;
   a contact lens conditioning means in one container of each pair;

a conditioning-counteracting solution in the other container of each pair;

cover means in sealing engagement with said parts of containers around the open tops thereof and capable of being peeled off said containers for opening the tops of said containers; and a lens handling implement sealed under siad cover means against said containers.

3. A disposable single-use contact lens conditioning package, comprising:

two pairs of adjacent open-topped containers of a size for accommodating a contact lens to be conditioned;

a contact lens conditioning means in one container of each pair;

a conditioning-counteracting solution in the other container of each pair;

cover means in sealing engagement with said pairs of containers around the open tops thereof and capable of being peeled off said containers for opening the tops of said containers; and a cover means holddown for holding said cover means in place over said containers and a lens handling implement, said cover means holddown and said lens handling implement being sealed under said cover means against said containers.

4. An assembly of disposable single-use contact lens conditioning packages, each package comprising:

two pairs of adjacent open-topped containers of a size for accommodating a contact lens to be conditioned;

a contact lens conditioning means in one container of each pair;

a conditioning-counteracting solution in the other container of each pair;

cover means in sealing engagement with said pairs of containers around the open tops thereof and capable of being peeled off said containers for opening the tops of said containers;

each package having opposite edges joined to corresponding edges of adjacent packages along a separable joint for forming said assembly; and a cover means holddown sealed under said cover means adjacent two of said containers in each of said packages in said assembly.

5. An assembly of disposable single-use contact lens conditioning packages, each package comprising:

two pairs of adjacent open-topped containers of a size for accommodating a contact lens to be conditioned;

a contact lens conditioning means in one container of each pair;

a conditioning-counteracting solution in the other container of each pair;

cover means ;in sealing engagement with said pairs of containers around the open tops thereof and capable of being peeled off said containers for opening the tops of said containers;

each package having opposite edges joined to corresponding edges of adjacent packages along a separable joint for forming said assembly; and a lens handling implement sealed under said cover means adjacent two of said containers in each of said packages in said assembly;

6. An assembly of disposable single-use contact lens conditioning packages, each package comprising:

two pairs of adjacent open-topped containers of a size for accommodating a contact lens to be conditioned;

a contact lens conditioning means in one container of each pair;

a conditioning-counteracting solution in the other container of each pair;

cover means in sealing engagement with said pairs of containers around the open tops thereof and capable of being peeled off said containers for opening the tops of said containers;

each package having opposite edges joined to corresponding edges of adjacent packages along a separable joint for forming said assembly; and a cover means holddown and a lens handling implement sealed under said cover means adjacent two of said containers in each of said packages in said assembly.

7. A package as claimed in claim 1 further comprising a cover means holddown having a bar portion with depending end portions each having a snap bead on the lower end thereof projecting inwardly under said bar portion for snapping over the edges of said containers with the bar portion over said cover means for holding said cover means in place over said containers.

* * * * *